United States Patent
Urban et al.

(10) Patent No.: US 9,883,851 B2
(45) Date of Patent: Feb. 6, 2018

(54) SYSTEM AND METHOD FOR SHEAR WAVE GENERATION WITH STEERED ULTRASOUND PUSH BEAMS

(71) Applicants: Matthew W. Urban, Rochester, MN (US); Alireza Nabavizadehrafsanjani, Rochester, MN (US); Pengfei Song, Rochester, MN (US); Shigao Chen, Rochester, MN (US); James F. Greenleaf, Rochester, MN (US)

(72) Inventors: Matthew W. Urban, Rochester, MN (US); Alireza Nabavizadehrafsanjani, Rochester, MN (US); Pengfei Song, Rochester, MN (US); Shigao Chen, Rochester, MN (US); James F. Greenleaf, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/663,866

(22) Filed: Mar. 20, 2015

(65) Prior Publication Data

US 2015/0265249 A1  Sep. 24, 2015

Related U.S. Application Data

(60) Provisional application No. 61/968,750, filed on Mar. 21, 2014.

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC ............ *A61B 8/485* (2013.01); *A61B 8/4494* (2013.01); *A61B 8/54* (2013.01); *G01S 7/52022* (2013.01); *G01S 7/52042* (2013.01); *G01S 15/8927* (2013.01); *G01S 15/8915* (2013.01)

(58) Field of Classification Search
CPC ...................................... A61B 8/485
USPC ......................................... 600/438
See application file for complete search history.

(56) References Cited

U.S. PATENT DOCUMENTS

| | | | | |
|---|---|---|---|---|
| 2003/0144591 A1* | 7/2003 | Smith | .................... | A61B 8/145 600/437 |
| 2005/0131298 A1* | 6/2005 | Cai | .................... | G01S 15/8925 600/447 |
| 2006/0058672 A1* | 3/2006 | Klepper | ................ | B06B 1/0622 600/447 |

OTHER PUBLICATIONS

Song, P., Comb-push Ultrasound Shear Elastography (CUSE): A Novel Method for Two-dimensional Shear Elasticity Imaging of Soft Tissues, IEEE Trans Med Imaging; 31(9):1821-1832, Sep. 2012.*

(Continued)

*Primary Examiner* — Rajeev Siripurapu
(74) *Attorney, Agent, or Firm* — Quarles & Brady LLP

(57) ABSTRACT

A system and method for performing a steered push beam (SPB) technique to create multiple foci generated by the interference of different ultrasound push beams to create shear waves and, based thereon, generate a report indicating mechanical properties about an object.

20 Claims, 11 Drawing Sheets

(56) References Cited

OTHER PUBLICATIONS

Song, P., Comb-push Ultrasound Shear Elastography (CUSE): A Novel and Fast Technique for Shear Elasticity Imaging, 2012 IEEE International Ultrasonics Symposium Proceedings (1842-1845) (2012).*

* cited by examiner

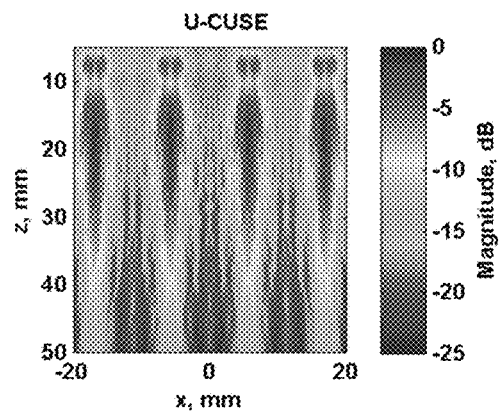 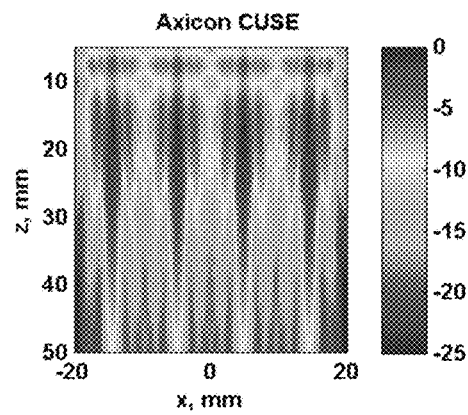
FIG. 5A    FIG. 5B
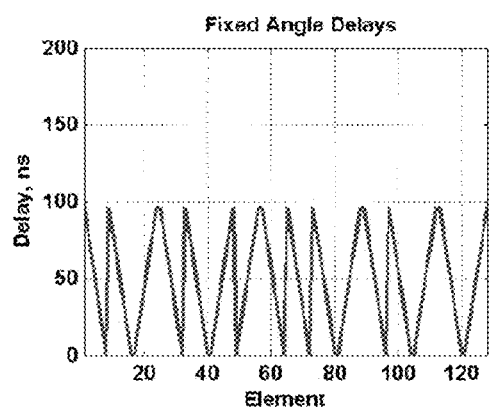 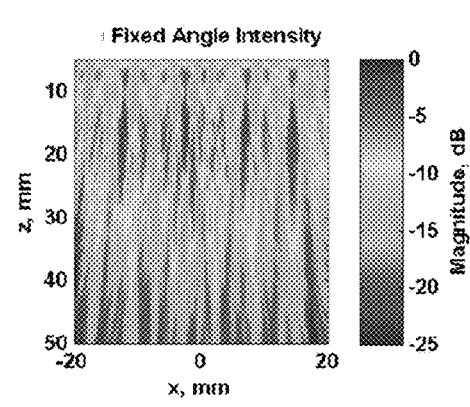
FIG. 6A    FIG. 6B
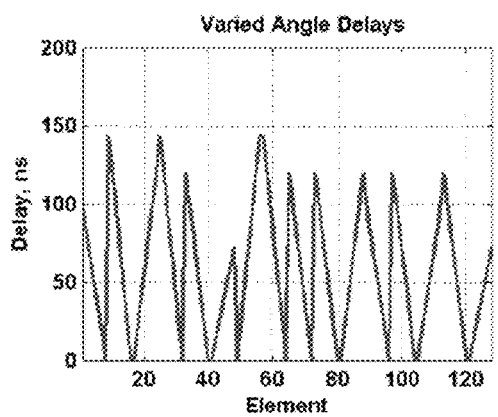 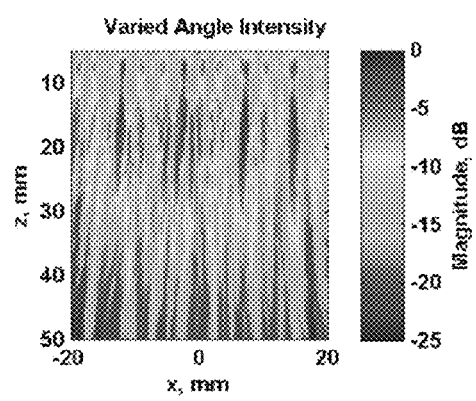
FIG. 7A    FIG. 7B

SYSTEM AND METHOD FOR SHEAR WAVE GENERATION WITH STEERED ULTRASOUND PUSH BEAMS

CROSS-REFERENCE TO RELATED APPLICATIONS

The present application is based on, claims priority to, and incorporates herein by reference, U.S. Provisional Application 61/968,750, filed Mar. 21, 2014, and entitled "SYSTEM AND METHOD FOR SHEAR WAVE GENERATION WITH STEERED ULTRASOUND PUSH BEAMS."

STATEMENT REGARDING FEDERALLY SPONSORED RESEARCH

This invention was made with government support under DK092255, and EB002167 awarded by the National Institutes of Health. The government has certain rights in the invention.

BACKGROUND

The present disclosure relates to systems and methods for ultrasound imaging. More particularly, disclosure relates to systems and methods for shear wave elastography using ultrasound.

SUMMARY

The present disclosure provides a system and method for performing a steered push beam (SPB) technique to create multiple foci generated by the interference of different ultrasound push beams to create shear waves. The push in the tissue results from conversion of the energy in the beam to an acoustic radiation force. The SPB method can use segments of an ultrasound aperture and apply steering angles to the segments to create overlapping beams that interfere to create a focal point that can have sufficient intensity to generate a shear wave. That is, an apodization can be applied relative to the plurality of transducer elements of the ultrasound system. Focused or unfocused push beams can be used and the steering angles can be assigned in a deterministic or random fashion. These systems and methods can be used with a variety of different hardware, including curved and phased one-dimensional array transducers and two-dimensional array transducers. A configuration that uses a subaperture of the transducer can be moved or steered further along the larger full aperture. The processes can be customized for particular locations in a desired field-of-view (FOV).

In accordance with one aspect of the disclosure, an ultrasound system is provided for measuring material mechanical properties of an object. The system includes an ultrasound transducer that includes a plurality of transducer elements and a processor. The processor is configured to assign an apodization relative to the plurality of transducer elements and, based on the apodization, operate the plurality of transducer elements to generate multiple ultrasound push beams to create interference in the object that creates multiple shear waves and associated multiple foci within the object. The processor is also configured to obtain shear wave elastography data from the object and calculate a mechanical property of the object using the obtained elastography data.

In accordance with another aspect of the disclosure, a method is provided for measuring a mechanical property of an object using an ultrasound system having an ultrasound transducer that includes a plurality of transducer elements. The method can include assigning an apodization relative to the plurality of transducer elements and, based on the apodization assigned, operating the plurality of transducer elements to generate multiple ultrasound push beams to create interference in the object that creates multiple shear waves and associated multiple foci within the object. The method can also include obtaining shear wave elastography data from the object and calculating a mechanical property of the object using the obtained elastography data.

In accordance with yet another aspect of the disclosure, an ultrasound system is provided for measuring material properties of an object. The system includes an ultrasound transducer that includes a plurality of transducer elements and a processor. The processor is configured to divide an aperture associated with the plurality of transducer elements into a plurality of segments. The processor is also configured to operate the plurality of transducer elements to generate multiple ultrasound push beams by energizing selected ones of the plurality of transducer elements based on the plurality of segments to create interference in the object that creates multiple shear waves and associated multiple foci within the object. The processor is further configured to obtain shear wave elastography data indicating mechanical properties of the object and generate a report indicating the mechanical properties of the object.

The foregoing and other aspects and advantages will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is a graphs showing intensity simulations for U-CUSE, where fields are normalized independently and are plotted on a log scale.

FIG. 5B is a graphs showing intensity simulations for axicon CUSE, where fields are normalized independently and are plotted on a log scale.

FIG. 6A is a graph showing results for a random configuration for the angle sign using a fixed $\theta=4$ degrees for transmit delays FIG. 6B is a graph showing results for a random configuration for the angle sign using a fixed $\theta=4$ degrees for the intensity field.

FIG. 7A is a graph showing results for a random configuration for the angle sign and random angles in the range θ=[3 degrees, 4 degrees, 5 degrees, 6 degrees], for transmit delays.

FIG. 7B is a graph showing results for a random configuration for the angle sign and random angles in the range θ=[3 degrees, 4 degrees, 5 degrees, 6 degrees], for intensity field.

DETAILED DESCRIPTION

Figure 1:
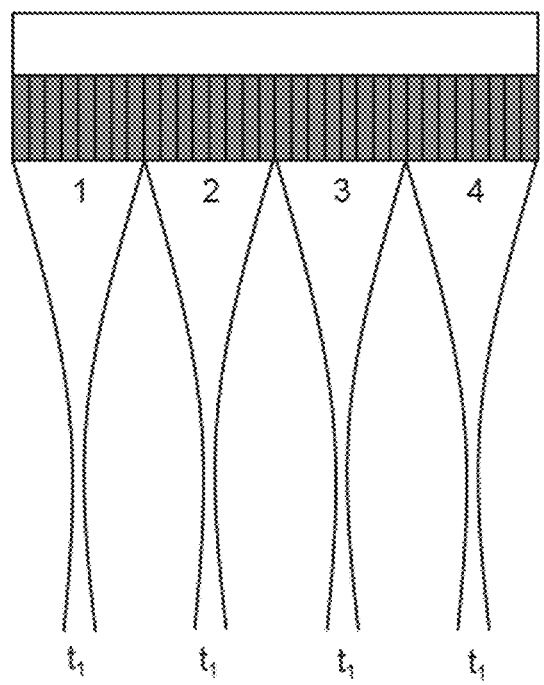
FIG. 1 is an illustration of a plurality of focused ultrasound push beams being simultaneously transmitted in a comb pattern.

As will be described, the present disclosure provides a system and method for performing a steered push beam (SPB) technique to create shear waves. Focused or unfocused push beams can be used and the steering angles can be assigned in a deterministic or random fashion. For example, co-pending U.S. patent application Ser. No. 14/001,604 describes systems and methods for creating and using unfocused beams and International Application No. PCT/US13/63631 describes systems and methods for creating and using focused beams. Each of these applications is incorporated herein by reference in its entirety. The present disclosure provides systems and methods for using multiple unfocused or focused push beams to generate multiple shear waves. As will be described, these shear waves can be used to determine elastic properties of the tissue through which the shear waves propagate. As a non-limiting example, such mechanical properties can include shear wave speed, shear wave attenuation, shear modulus, shear viscosity, storage modulus, loss modulus, Young's modulus, bulk modulus, mechanical relaxation time, and the like. Thus, the present disclosure provides systems and methods for performing a SPB technique to create shear waves that can be used to obtain elastography data from the object. The obtained elastography data can then be used to calculate a mechanical property of the object, which may include, as a non-limiting example, shear wave speed, shear wave attenuation, shear modulus, shear viscosity, storage modulus, loss modulus, Young's modulus, bulk modulus, mechanical relaxation time, and the like.

To best understand the present disclosure, a discussion of push beam generation is provided. As will be set forth, both focused and unfocused push beams will be described. Following thereafter, the present disclosure will set forth systems and methods for SPB.

When an ultrasound push beam is transmitted into an object, shear waves are generated and propagate outward from the push beam in opposite directions. Consequently, shear waves are not generated in the push beam region, which means that shear wave speeds cannot be measured in the region where the push beam is generated. In addition, shear waves produced by an ultrasound push beam attenuate quickly over a short propagation distance. As a result, shear waves produced by a single push beam can only image a small region-of-interest; thus, in these instances, multiple push-detect acquisitions are required to piece together an image with large field-of-view ("FOV").

As described in the above-referenced, co-pending US application, entitled "Ultrasound Vibrometry with Unfocused Ultrasound," a comb-shaped set of unfocused ultrasound beams can be used to provide a full FOV, two-dimensional shear wave speed map together with one rapid data acquisition. This method is referred to as comb-push ultrasound shear elastography ("CUSE").

In CUSE, multiple unfocused ultrasound push beams are used to produce shear waves within a tissue for shear wave elasticity imaging. Only one subset of transducer elements is used for each push beam; thus, multiple subsets of elements can be used for different spatial locations to simultaneously transmit multiple push beams. In CUSE, shear waves produced by each push beam can be treated as an independent realization of a single push beam.

Using CUSE, shear waves from different push beams interfere with each other and eventually fill the entire field-of-view ("FOV"). To achieve robust shear wave speed estimation, a directional filter can be used to extract left-to-right ("LR") propagating shear waves and right-to-left ("RL") propagating shear waves from the interfering shear wave patterns. A time-of-flight based shear wave speed estimate method may be used to recover local shear wave speed at each pixel from both LR waves and RL waves. A final shear wave speed map may then be combined from the LR speed map and RL speed map. Because comb-push pulses produce shear wave motions with high amplitude at all image pixels, including at the push beam areas, both shear wave speed at the "source free" areas and shear wave speeds at the push beam areas can be recovered.

Thus, CUSE enables a full FOV two-dimensional reconstruction of a shear elasticity map with only one data acquisition. To improve acoustic radiation force penetration and generate stronger shear waves into deeper tissue (i.e., liver and kidney), the previous CUSE method can be modified using focused ultrasound push beams. Using focused ultrasound push beams facilitates the generation of strong shear waves at locations deep within tissues. This ability to generate strong shear waves at deep tissue locations can lead to higher SNR for shear wave elasticity imaging compared to CUSE with unfocused beams.

However, as described in the above-referenced, co-pending PCT Application, CUSE may also be performed with focused beams. In one configuration, illustrated in FIG. 1, the transducer elements are divided into a number of subgroups, such as four subgroups, that each simultaneously transmits a focused ultrasound beam. This technique is referred to as focused CUSE, or "F-CUSE." As noted, in F-CUSE, the transducer elements are divided into a number, N, of subgroups, with each subgroup containing one or more transducer elements.

As one example of the F-CUSE technique, a 128 element ultrasound transducer can be divided into four subgroups of 32 transducer elements each. In F-CUSE, all subgroups transmit focused ultrasound beams simultaneously to form a comb-push pattern ultrasound field. In one example, the duration of the push pulse beams can be on the order of 600 μs.

In another configuration, the transducer elements are divided into a number of subgroups with overlapping elements, and the subgroup that is used to transmit an ultrasound beam is rapidly changed along the lateral direction. The result of this "marching" of the subgroup of transducer elements being energized is to provide a focused ultrasound push beam at successively different horizontal locations. This technique may be referred to as marching CUSE, or "M-CUSE."

Figure 2:
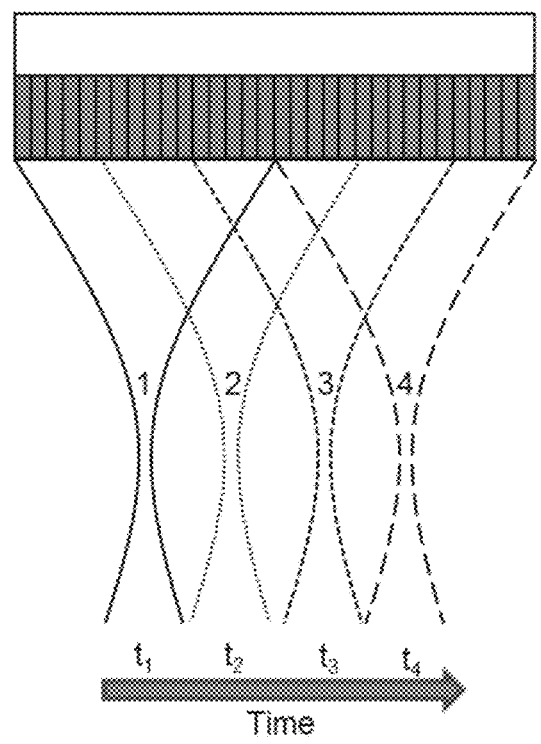
FIG. 2 is an illustration of a focused ultrasound push beam that is rapidly translated along a lateral direction to generate shear waves.

As one example of the M-CUSE technique, shown in FIG. 2, a 128 element ultrasound transducer can be divided into four, overlapping subgroups of 64 elements each. The first subgroup then transmits a single, focused push beam at a first time, t1. The duration of this push beam can be shorter than would be used in F-CUSE or traditional CUSE if it is desirable to control tissue or transducer heating due to repeated transmission using the overlapping transducer elements. As an example, the push beam duration in M-CUSE can be on the order of 200 μs. The push beam duration is selected based on considerations for how much overlap there is between subgroups of the transducer elements. For instance, the duration can be selected such that any given transducer element in overlapping subgroups is not energized for a consecutive duration that may lead to overheating in that element.

After the first push beam is transmitted, a second push beam is transmitted at a second time, $t_2$, using the second subgroup of elements. This continues for the third and fourth subgroups. There is typically a small duration between consecutive push beams. For example, there can be a 15 μs delay between consecutive push beams. In this short duration of time, shear waves will propagate in soft tissue only about 0.45 mm, which is about 1.5 times the size of an individual transducer element in the transducer. Thus, in general, the amount of shear wave propagation between successive push beams is negligible for all subgroups after transmitting all of the focused push beams.

Figure 3:
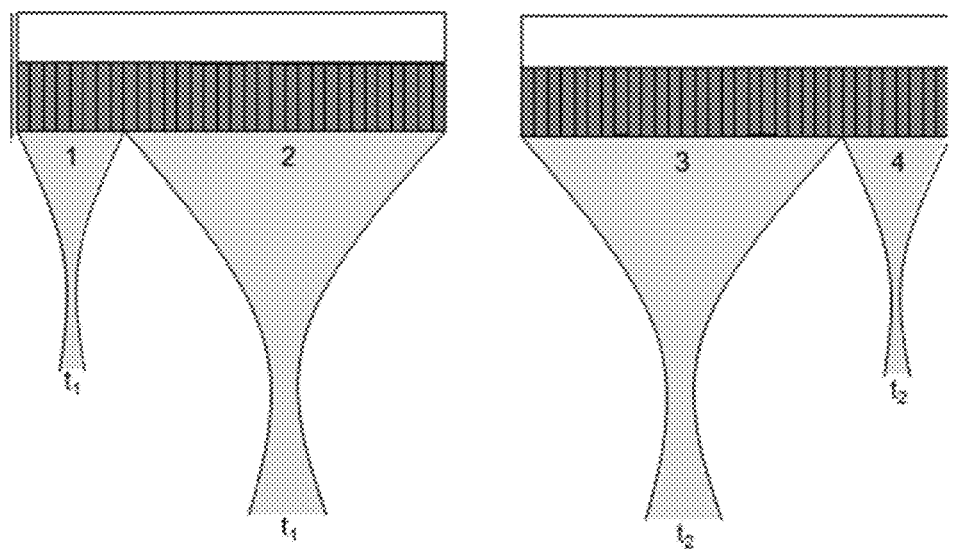
FIG. 3 is an illustration of a plurality of focused ultrasound push beams being simultaneously transmitted, in which each of the ultrasound push beams is generated with different sized subgroups of transducer elements.

It is noted that each push beam of the F-CUSE or M-CUSE techniques may have a different number of transmit elements and may be focused at different depths. Additionally, each of the push events for the M-CUSE technique may include using more than one push beams. In the example shown in FIG. 3, push beams 1 (with less elements) and 2 (with more elements) are simultaneously transmitted at time t1, followed by push beams 3 and 4 transmitted simultaneously at time t2. This combination push will produce strong shear waves at all depths and all lateral positions for shear wave detection and processing. It is also noted that push beams in M-CUSE can have different push durations and can be transmitted in an arbitrary order (for example, in a different order 1→4→3→2 compared to the order 1→2→3→4 illustrated in FIG. 2).

Similar to the original CUSE method, both F-CUSE and M-CUSE can generate comb-patterned ultrasound push beams that induce a complicated shear wave field with interferences. Directional filtering described by Manduca et al. in "Spatio-Temporal Directional Filtering for Improved Inversion of MR Elastography Images," *Medical Image Analysis*, 2003; 7(4): 465-473, can thus be used to separate the shear waves into multiple directions without interference so that robust shear wave estimates can be achieved at each imaging pixel within the FOV.

After comb-push transmission, a plane wave imaging mode can be used with all transducer elements delivering ultrasound to detect the propagating shear waves. Alternatively, the detection scheme described above can also be used.

With this description of systems and methods for focused or unfocused push beams in place, we turn our attention to the present disclosure, which includes system and method for performing a steered push beam (SPB) technique to create multiple foci generated by the interference of different ultrasound push beams to create shear waves.

Consider an ultrasound array transducer, either one-dimensional array or two-dimensional array. For simplicity of discussion, consider the one-dimensional array case. However, this choice is non-limiting and the following description can be extended to two-dimensional arrays. The aperture of the array transducer consists of N elements. This aperture can be divided into segments of $N_s$ elements. Each segment can be assigned an apodization, which assigns a weight to the amplitude of signals applied to the elements in the segment, steering angle with either positive or negative signed inclination, as well as focusing delays for a focused beam. A subaperture of the transducer can be designed and moved, such as in the M-CUSE method, or collectively steered further along the larger full aperture.

For discussion purposes the following will primarily concentrate the descriptions to the use of unfocused beams, such as described above, but focused beams can be used. These parameters can be determined in a manner to create specific types of beams or configurations, or the parameters can be left for random assignment. As follows, both deterministic and random configurations will be described.

Deterministic Configurations

Figure 4A:
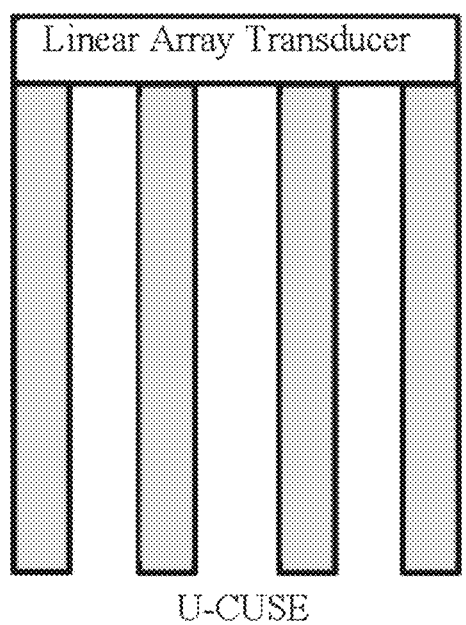
FIG. 4A is a schematic drawing illustrating a U-CUSE method.
Figure 4B:
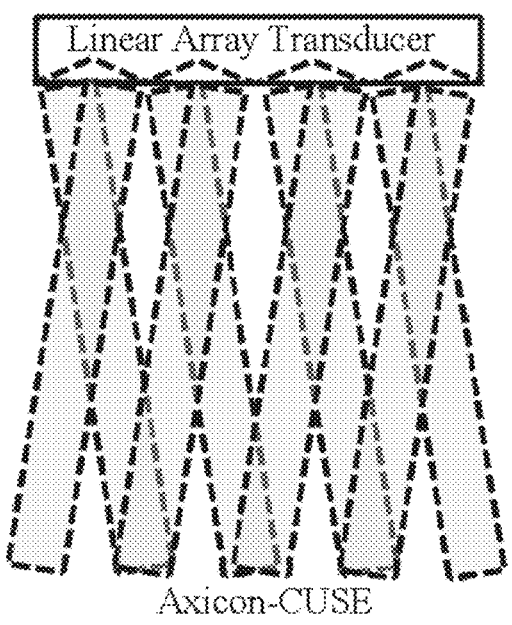
FIG. 4B is a schematic drawing illustrating an axicon CUSE method.

It may be desirable to mimic certain configurations. For example the above-described CUSE method employs push beams that are deterministically placed in the field-of-view (FOV) to create shear waves from known positions. With steering beams can be generated in specified positions, as shown in FIG. 4B.

Such an arrangement can be compared between an unfocused CUSE (U-CUSE) configuration and so-called axicon CUSE (AxCUSE) configuration because one of the beams is formed with an axicon-like arrangement using the steering of +θ and −θ for adjacent segments of elements. The acoustic radiation force density, F, in an absorbing medium can be written as:

$$F = \frac{2\alpha I}{c}; \qquad (6)$$

where α is the ultrasound attenuation of the medium, I is the ultrasound intensity, and c is the ultrasound speed in the medium. The force is proportional to the intensity, so the radiation force distribution can be explored by simulating the ultrasound intensity using a simulation package such as Field II. A simulation of the U-CUSE configuration depicted in FIG. 4A and the axicon CUSE configuration depicted in FIG. 4B are shown in FIG. 5 for unfocused beams of $N_s$=16 elements and using θ=3 degrees. A linear array transducer mimicking the L7-4 transducer (Philips Healthcare, Andover, Mass.) was used for the simulations with an ultrasound frequency of 4.0 MHz.

Many parameters such as the number of elements, angle of inclination, positions of beam segments, ultrasound frequency, medium ultrasound attenuation, and transducer geometry can be varied to control the ultrasound intensity distribution for specific applications. Simulations of the intensity distributions can be used to explore this wide parameter space for desired configurations.

Randomized Configurations

In the previous examples not all segments were used. It may be desirable to use more elements to improve energy deposition in the medium. Additionally, it may be advantageous to generate multiple shear wave sources in the FOV for the purposes of creating a plurality of shear waves that are propagating in the medium. Shear wave attenuation in some materials or tissues can be quite significant so shear wave sources may be spaced too far apart to generate shear waves in certain areas in the FOV. Increasing the number of shear wave sources in the FOV provides a higher probability that all areas of the FOV will encounter a propagating shear wave that can be used for later analysis to estimate shear wave velocity or other parameters related to material characterization of elasticity or viscoelasticity.

Another consideration is that the acoustic output for push beams can be very high. These levels are regulated by the Food and Drug Administration (FDA). To reduce the peak levels of pressure a wider distribution of the ultrasound pressure in the FOV may help to avoid having to reduce input voltage levels and achieve maximum power deposition for shear wave imaging.

As an example, let the total number of elements N=128 and the number of elements in a segment $N_s$=8. For each segment an angle of inclination can be assigned as either $+\theta$ or $-\theta$. In this example let $\theta$=4 degrees. The sign of the angle can be randomly assigned such that the signs for each of the segments may be [--+--++---+--+-+]. The sign of the segments can be determined using a random number generator with a starting seed value applied to the number generator so that previously used seeds can be used to obtain the same result with subsequent simulations. The time delays applied to the aperture and the resulting ultrasound intensity field are shown in FIG. 6.

In the previous example, the value of $\theta$ was fixed and only the sign was allowed to randomly change. Additionally, the value of $\theta$ could be allowed to vary over a specified range of values to change the distribution of the intensity in the FOV. The values of $\theta$ were allowed to vary over [3 degrees, 4 degrees 5 degrees, 6 degrees].

An example of the time delays and resulting ultrasound intensity field is shown in FIG. 7 with the following values for the segments [−4 degrees, −6 degrees, +6 degrees, −6 degrees, −5 degrees, +3 degrees, +6 degrees, −6 degrees, −5 degrees, −5 degrees, +5 degrees, −5 degrees, −5 degrees, +5 degrees, −5 degrees, +3 degrees].

To evaluate optimal fields, an automated method was designed to determine how many foci were created at a given depth in the FOV. For a given intensity field a region in depth was averaged together (a few millimeters). For each averaged profile, $I_n(x,z)$ the equation is:

$$I_m(x, z) = I_n^2(x, z) - \overline{I_n^2(x, z)}; \text{ and} \quad (7)$$

$$\overline{I_n^2(x, z)} = \frac{1}{N_x} \sum_{x=1}^{N_x} I_n^2(x, z); \quad (8)$$

where $\overline{I_n^2(x,z)}$ is the mean of the squared average profile. A spatial Fourier transform is then taken on the signal $I_m(x, z)$ and the peak spatial frequency was evaluated. More peaks in the $I_m(x,z)$ signal will translate into higher spatial frequencies. The spatial peak frequency indices are stored and then summed over the depths of interest. This sum can be compared against the sums from other configurations. The sum over a specified depth range can be used as the optimization metric. The starting seed value for the random number that generated the maximal sums can be stored for later use in implementing the optimal configuration.

Experiments

Simulations were performed in Field II to determine optimal random configurations. The L7-4 transducer geometry was used with an ultrasound frequency of 4 MHz, $\alpha$=0.5 dB/cm/MHz, N=128, $N_s$=8. The AxCUSE cases were implemented with $\theta$=3 degrees, 4 degrees, 5 degrees. Each tooth used 32 elements. In one case, we fixed $\theta$=3 degrees, 4 degrees, 5 degrees, 6 degrees, 7 degrees, or 8 degrees and only allowed the sign of the angle to be randomly assigned. In another case, we used ranges of $\theta$=3-6 degrees and $\theta$=4-7 degrees and allowed both the sign and the angle to be randomly assigned. Starting seed values were used that ranged from 0-100 in MATLAB (The MathWorks, Natick, Mass.) for the random number generators. The algorithm described above was used to find the optimal configurations for each case and tested them in elastic tissue-mimicking phantoms. The optimal configurations were used on the Verasonics V-1 system (Verasonics, Inc., Redmond, Wash.). These configurations were tested in a homogeneous phantom with a shear wave velocity of $c_s$=1.55 m/s (CIRS, Inc., Norfolk, Va.) and phantoms with spherical and cylindrical inclusions of different sizes (Models 049 and 049A, CIRS, Inc., Norfolk, Va.). A 400 µs toneburst was used to produce the acoustic radiation force. After the push was completed compound plane wave imaging was used with three angles (−4 degrees, 0 degrees, 4 degrees) for shear wave motion tracking. In-phase/quadrature (IQ) data was saved from the Verasonics. One-dimensional autocorrelation was used to estimate the particle velocity from the IQ data.

The data was processed in a manner similar to data acquired using CUSE. Directional filters were applied to extract the left-to-right (LR) and right-to-left (RL) propagating waves. A two-dimensional shear wave velocity calculation algorithm was used to estimate the shear wave velocity at each location. For example, co-pending U.S. Application Ser. No. 61/856,452 discusses calculations of wave fields for the 2D shear wave velocity, which is incorporated herein by reference in its entirety. The shear wave velocity maps from the LR and RL waves were combined similar to the method described by Song, et al. (P. Song, H. Zhao, A. Manduca, M. W. Urban, J. F. Greenleaf, and S. Chen, "Comb-push ultrasound shear elastography (CUSE): a novel method for two-dimensional shear elasticity imaging of soft tissues," IEEE Trans. Med. Imaging, vol. 31, pp. 1821-1832, 2012, which is incorporated herein by reference in its entirety) for CUSE. Additionally, quality control metrics could be applied in the combination process including but not limited to shear wave energy, normalized cross-correlation coefficient from the shear wave velocity estimation, or local image standard deviation of the shear wave velocity maps.

In addition to the random configurations, U-CUSE and focused CUSE (F-CUSE) configurations were also applied. The U-CUSE configuration used 4 teeth of 16 elements separated by 22 elements. The F-CUSE configurations used 4 teeth with 32 elements for each tooth and focal depths of 20, 25, and 30 mm.

Figure 8:
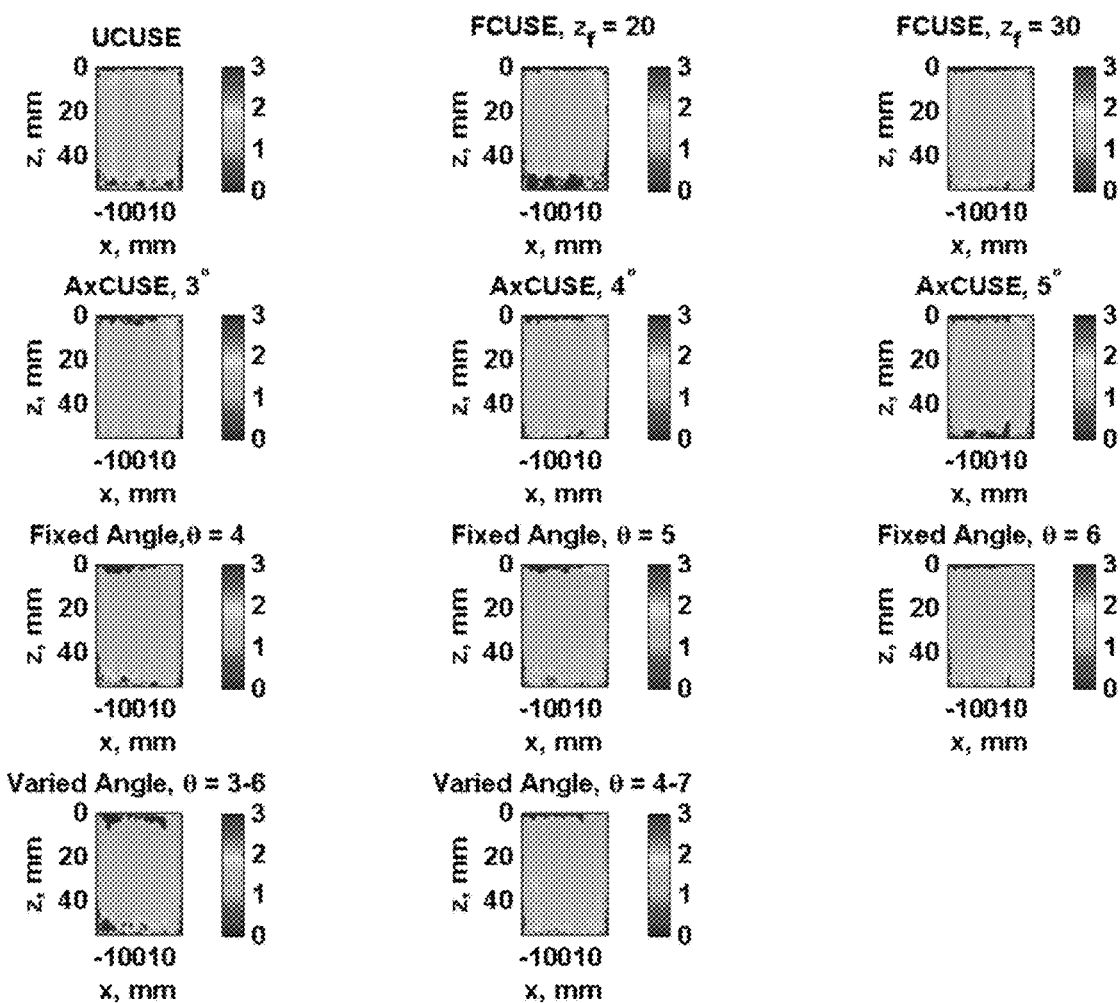
FIG. 8 is a set of graphs showing homogeneous phantom results.
Figure 9:
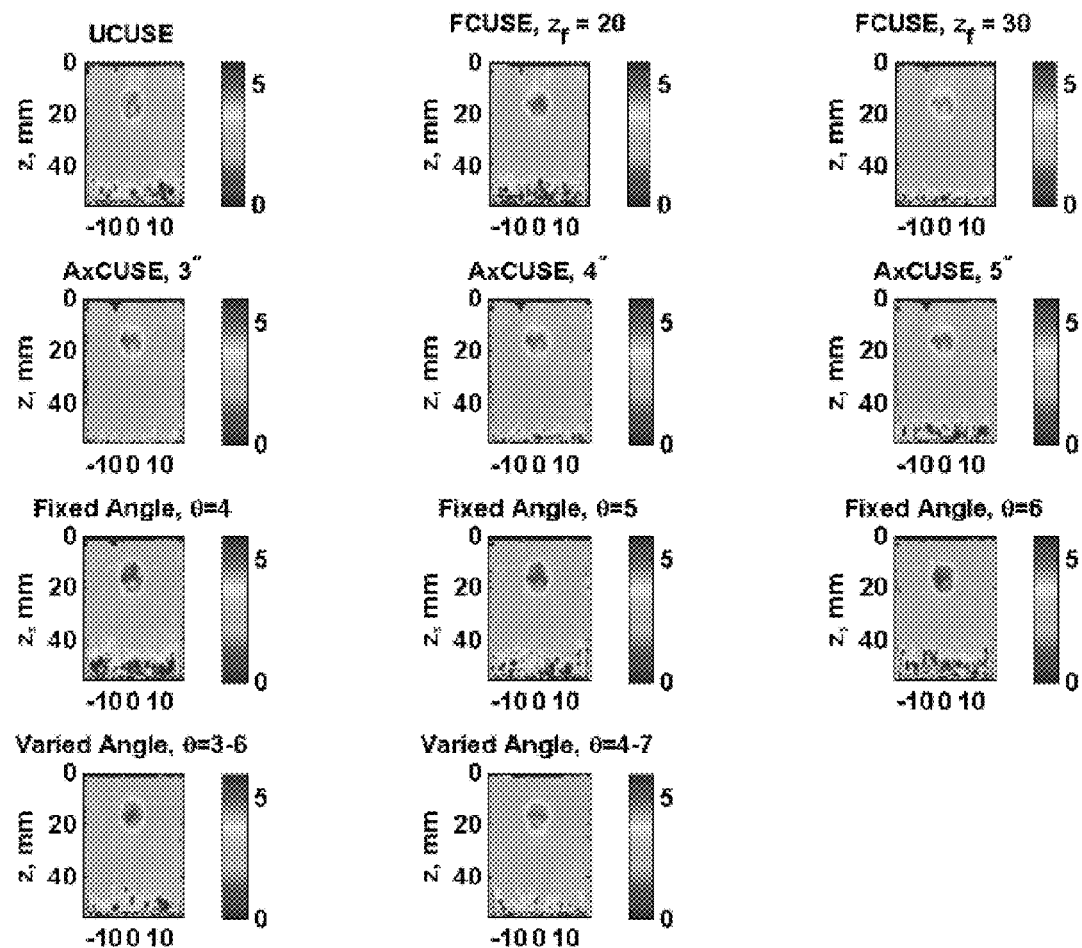
FIG. 9 is a set of graphs showing inclusion phantom results with 10 mm spherical inclusion.
Figure 10:
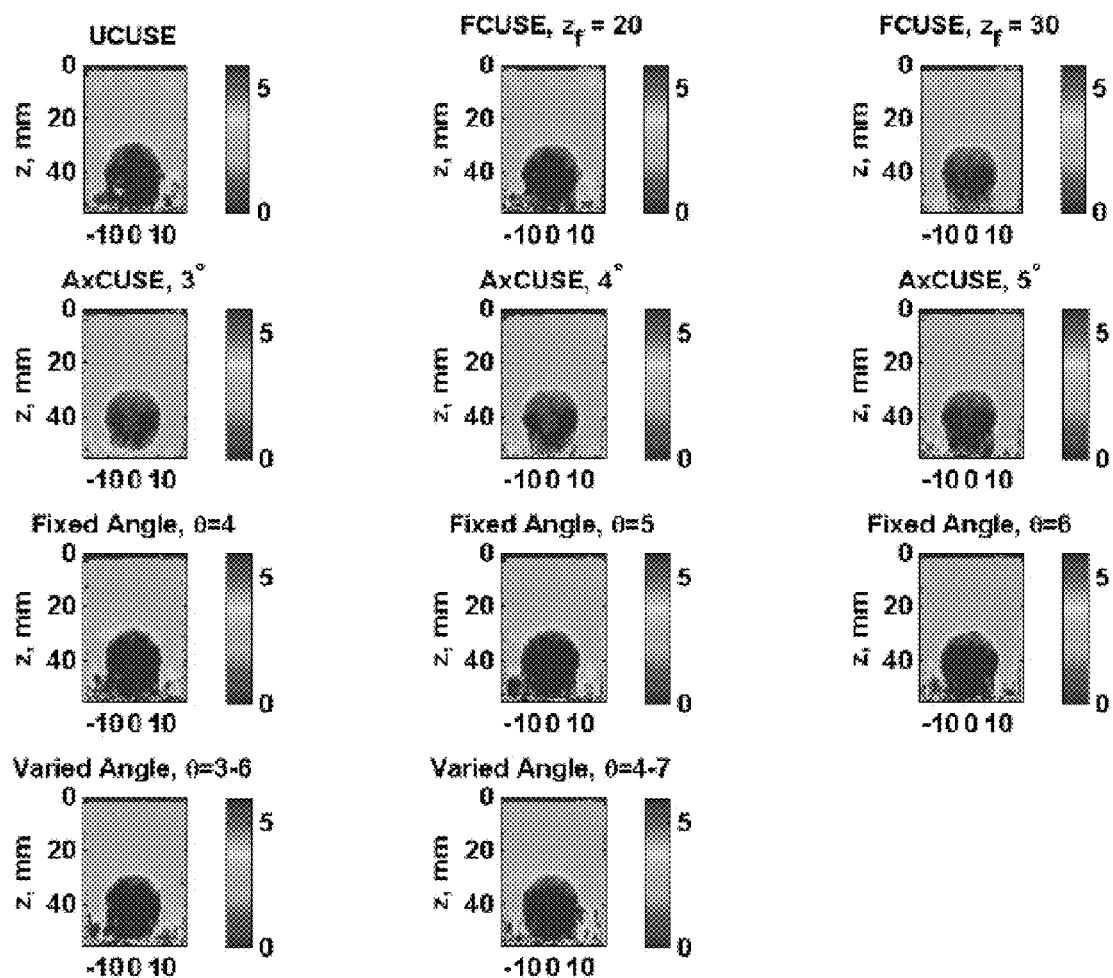
FIG. 10 is a set of graphs showing inclusion phantom results with 20 mm spherical inclusion.
Figure 11:
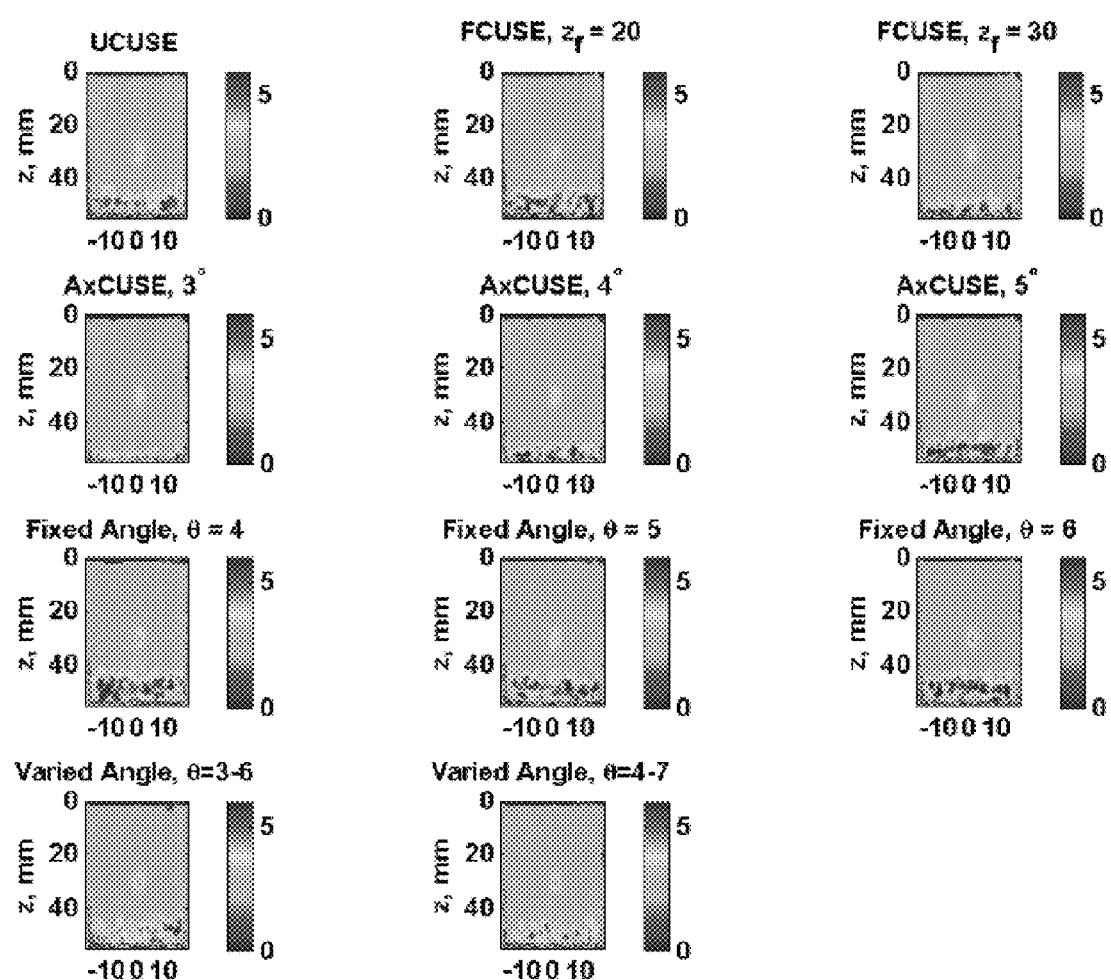
FIG. 11 is a set of graphs showing inclusion phantom results with 4.1 mm cylindrical inclusion.
Figure 12:
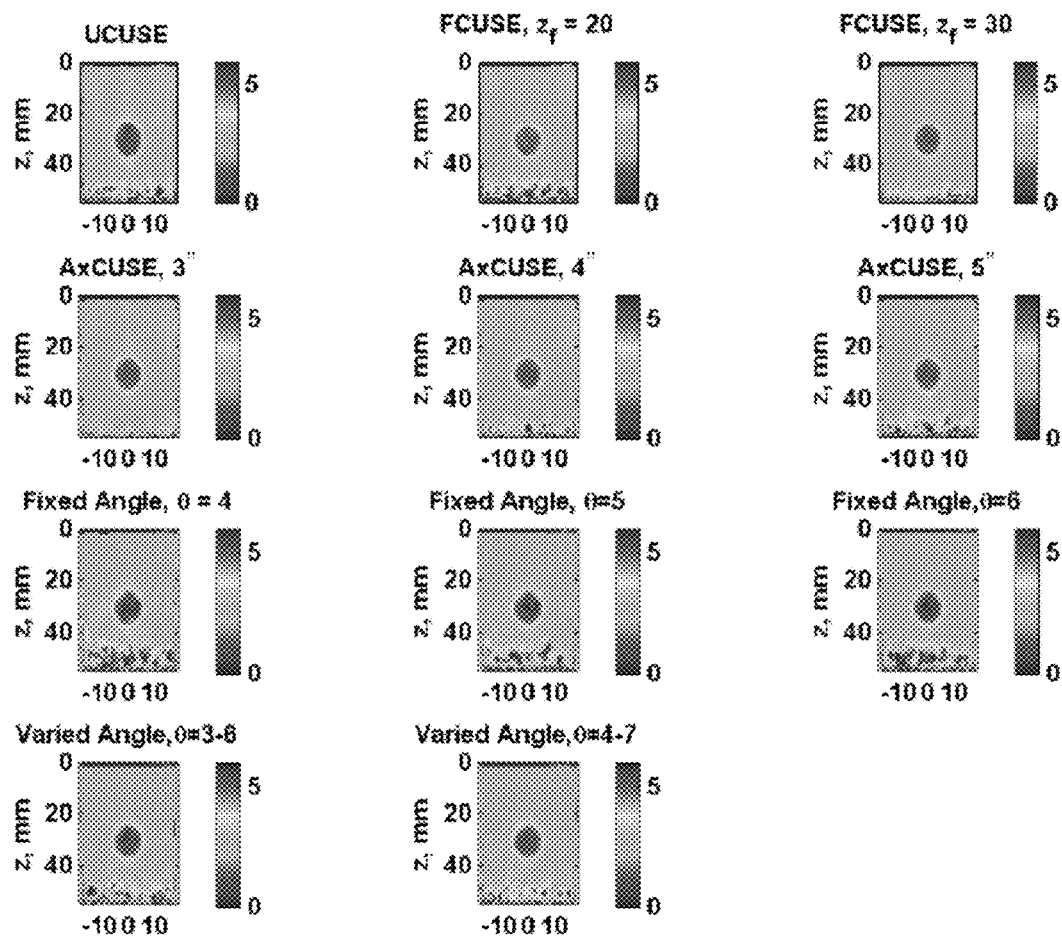
FIG. 12 is a set of graphs showing inclusion phantom results with 10.4 mm cylindrical inclusion.

Results for the homogeneous phantom with multiple configurations are shown in FIG. 8. Table 1 following below gives the mean and standard deviations for the shear wave velocities measured in the homogeneous phantoms from a large square region-of-interest (ROI) centered in the images.

TABLE 1

| Configuration | Shear Wave Velocity, m/s |
| --- | --- |
| U-CUSE | 1.49+/−0.07 |
| F-CUSE, $Z_f$ = 20 mm | 1.57+/−0.05 |
| F-CUSE, $Z_f$ = 20 mm | 1.47+/−0.04 |
| Axicon CUSE, θ = 3 degrees | 1.47+/−0.04 |
| Axicon CUSE, θ = 4 degrees | 1.44+/−0.04 |
| Axicon CUSE, θ = 5 degrees | 1.51+/−0.04 |
| Fixed Angle, θ = 4 degrees | 1.52+/−0.05 |
| Fixed Angle, θ = 5 degrees | 1.50+/−0.05 |
| Fixed Angle, θ = 6 degrees | 1.44+/−0.06 |
| Varied Angle, θ = 3-6 degrees | 1.57+/−0.13 |
| Varied Angle, θ = 4-7 degrees | 1.48+/−0.05 |

The configurations were applied in the CIRS 049 phantom on the Type IV spherical inclusions of diameters of 10 and 20 mm. The background material of the CIRS 049 phantom has a Young's modulus of 25 kPa and the Type IV material has a Young's modulus of 80 kPa. The corresponding shear wave velocities of the background and inclusion materials are 2.89 and 5.16 m/s, respectively. The CIRS 049A phantom has cylindrical inclusions of different diameters. The inclusions were imaged with diameters of 4.1 and 10.4 mm. The background and inclusion materials have shear wave velocities of 3.11 and 5.16 m/s, respectively. The results for the inclusion phantoms with multiple configurations are shown in FIGS. 9-12 for the spherical inclusion with 10 mm diameter, the spherical inclusion with 20 mm diameter, the cylindrical inclusion with 4.1 mm diameter, and the cylindrical inclusion with 10.4 mm, respectively.

Table 2 following below gives the mean and standard deviations for the shear wave velocities measured in the background and inclusions.

| Configuration | 10 mm Spherical Inclusion | | | 20 mm Spherical Inclusion | | | 4.1 mm Cylindrical Inclusion | | | 10.4 mm Cylindrical Inclusion | | |
| --- | --- | --- | --- | --- | --- | --- | --- | --- | --- | --- | --- | --- |
| | $c_B$, m/s | $c_I$, m/s | CNR | $c_B$, m/s | $c_I$, m/s | CNR | $c_B$, m/s | $c_I$, m/s | CNR | $c_B$, m/s | $c_I$, m/s | CNR |
| U-CUSE | 2.78 | 4.21 | 11.29 | 2.90 | 6.40 | 18.00 | 2.91 | 3.67 | 14.69 | 2.94 | 4.88 | 18.52 |
| F-CUSE, $z_f$ = 20 mm | 2.82 | 4.25 | 13.83 | 2.82 | 6.41 | 20.86 | 2.78 | 3.45 | 17.11 | 2.87 | 4.59 | 20.52 |
| F-CUSE, $z_f$ = 30 mm | 2.72 | 4.05 | 11.21 | 2.81 | 5.38 | 17.72 | 2.80 | 3.65 | 22.28 | 2.90 | 4.66 | 22.02 |
| Axicon CUSE, θ = 3° | 2.73 | 4.21 | 12.17 | 2.82 | 5.39 | 17.75 | 2.83 | 3.64 | 20.58 | 2.89 | 4.68 | 23.07 |
| Axicon CUSE, θ = 4° | 2.73 | 4.19 | 12.38 | 2.80 | 5.52 | 20.10 | 2.81 | 3.66 | 21.95 | 2.87 | 4.70 | 25.94 |
| Axicon CUSE, θ = 5° | 2.76 | 4.17 | 12.16 | 2.80 | 5.58 | 20.53 | 2.81 | 3.59 | 19.80 | 2.86 | 4.69 | 27.69 |
| Fixed Angle, θ = 4° | 2.85 | 4.55 | 16.55 | 2.81 | 7.27 | 25.08 | 2.84 | 3.76 | 18.74 | 2.81 | 4.93 | 35.27 |
| Fixed Angle, θ = 5° | 2.81 | 4.50 | 13.99 | 2.80 | 7.41 | 30.10 | 2.82 | 3.75 | 20.21 | 2.81 | 4.95 | 43.26 |
| Fixed Angle, θ = 6° | 2.75 | 4.58 | 13.92 | 2.78 | 7.14 | 31.86 | 2.78 | 3.84 | 25.20 | 2.79 | 4.96 | 44.46 |
| Varied Angle, θ = 3-6° | 2.80 | 4.37 | 13.27 | 2.79 | 6.80 | 27.47 | 2.79 | 3.75 | 16.71 | 2.79 | 4.88 | 48.90 |
| Varied Angle, θ = 4-7° | 2.79 | 4.22 | 10.87 | 2.79 | 6.81 | 24.5 | 2.80 | 3.73 | 17.07 | 2.79 | 4.82 | 45.99 |

Additionally, the contrast-to-noise ratio (CNR) was computed for each inclusion and is listed in Table 2 as well for the different configurations. The CNR was calculated as:

$$CNR = \frac{|\mu_I - \mu_B|}{\sigma_B}; \qquad (9)$$

where $\mu_I$ and $\mu_B$ are the mean shear wave velocity values in the inclusion (I) and background (B), respectively, and $\sigma_B$ is the standard deviation of the shear wave velocity values in the background.

Discussion

The image results show that the methods based on using steered push beams can make shear wave velocity images similar to those made by the U-CUSE and F-CUSE implementations. In the homogeneous phantoms, the variation for the SPB implementations were generally on the same order or better than those measured with U-CUSE or F-CUSE. The SPB methods demonstrated a uniform shear wave velocity measurement with depth in many cases.

The images taken of the various inclusions showed the SPB methods could provide good depictions of the inclusions. In particularly, the Axicon CUSE implementation with θ=3 degrees can show the bottom of the inclusion that none of the other configurations can provide. The CNR was also found to be equivalent or in many cases better for the SPB configurations as compared to the CUSE results. It is also evident that certain configurations can image inclusions of different sizes and at different depths more optimally than others. One explanation for this may be that the SPB method generates shear waves with many different propagating directions which may achieve a shear compounding effect that improves the signal-to-noise ratio (SNR) and the shape of the inclusions. In this sense, optimal configurations could be adopted for certain applications.

These results were obtained with steered unfocused push beams so they could be compared against the results of U-CUSE. Using all the elements in the aperture can provide better shear wave coverage over the FOV. Also, a subaperture of the transducer can be used and moved or steered further along the larger full aperture. This is similar to the marching CUSE method. The depth-of-field (DOF) defined as the point where the noise in the shear wave velocity map increases substantially is higher for the SPB configurations compared to that for U-CUSE and is comparable in many cases to the performance of F-CUSE.

This method provides a large amount of flexibility for configuring the arrangements of the steered beams and the present optimization criteria can be used, or the optimization metric could be adjusted for specific applications. Additionally, focused beams could be used with larger segments to concentrate energy in certain regions.

Thus, as described, steered push beams can be used in deterministic or randomized configurations to produce high quality shear elasticity maps. The results shown in this disclosure demonstrate that uniformity and depth-of-field for shear wave speed maps compare equivalently or better than CUSE implementations. The SPB method is very flexible and could be optimized for a wide spectrum of clinical applications.

Figure 13:
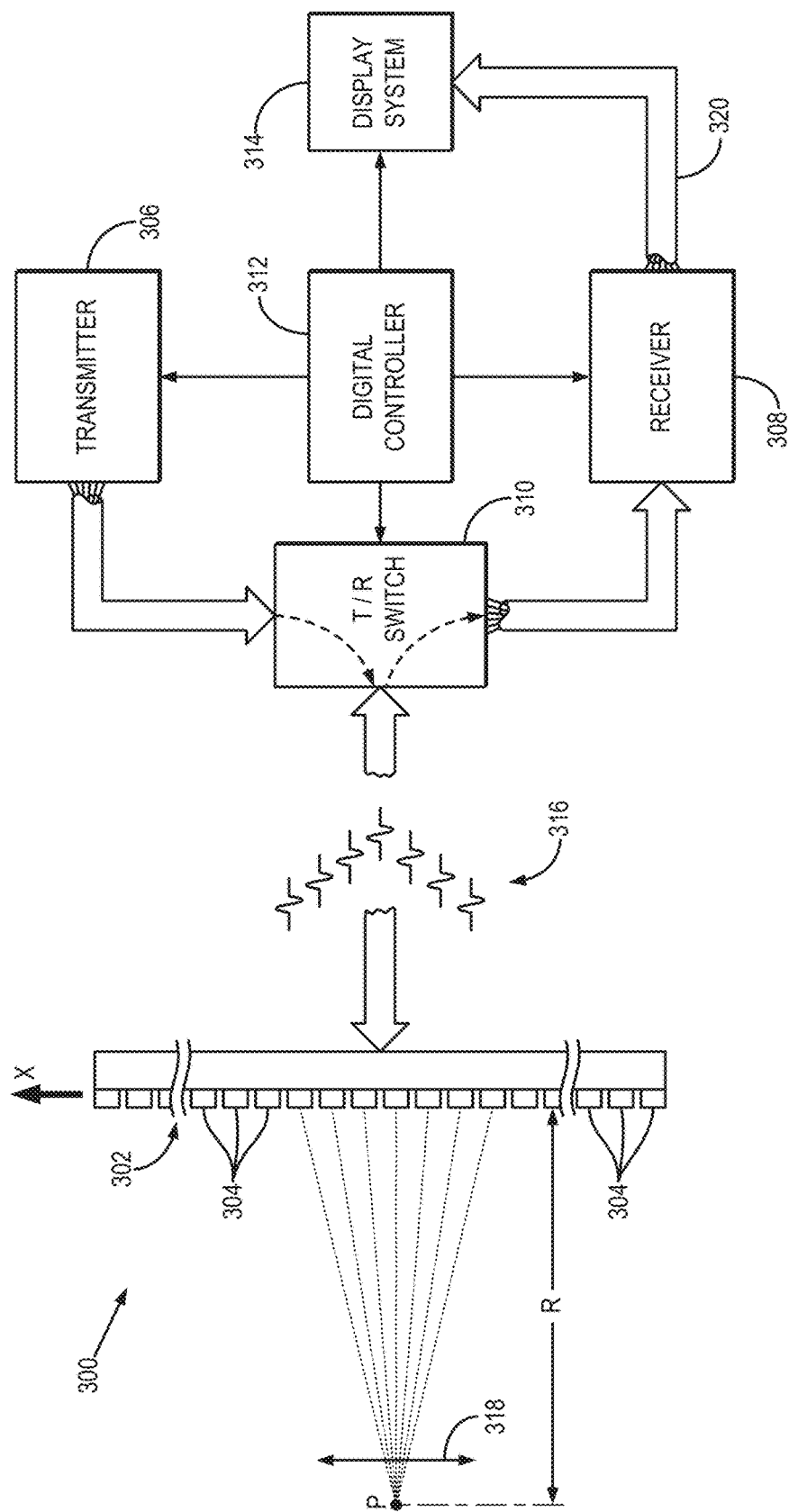
FIG. 13 is a schematic diagram of an ultrasound system that may be configured to operate in accordance with the present disclosure.

Referring now to FIG. 13, an example of an ultrasound imaging system 300 that may be used with the present invention is illustrated. It will be appreciated, however, that other suitable ultrasound systems can also be used to implement the present invention. As a non-limiting example, the above-described systems and methods are applicable on curved and phased one-dimensional array transducers and two-dimensional array transducers. The ultrasound imaging system 300 includes a transducer array 302 that includes a plurality of separately driven transducer elements 304. When energized by a transmitter 306, each transducer element 302 produces a burst of ultrasonic energy. The ultrasonic energy reflected back to the transducer array 302 from the object or subject under study is converted to an electrical signal by each transducer element 304 and applied separately to a receiver 308 through a set of switches 310. The transmitter 306, receiver 308, and switches 310 are operated under the control of a digital controller 312 responsive to the commands input by a human operator. A complete scan is performed by acquiring a series of echo signals in which the switches 310 are set to their transmit position, thereby directing the transmitter 306 to be turned on momentarily to energize each transducer element 304. The switches 310 are then set to their receive position and the subsequent echo signals produced by each transducer element 304 are measured and applied to the receiver 308. The separate echo signals from each transducer element 304 are combined in the receiver 308 to produce a single echo signal that is employed to produce a line in an image, for example, on a display system 314.

The transmitter 306 drives the transducer array 302 such that an ultrasonic beam is produced, and which is directed substantially perpendicular to the front surface of the transducer array 302. To focus this ultrasonic beam at a range, R, from the transducer array 302, a subgroup of the transducer elements 304 are energized to produce the ultrasonic beam and the pulsing of the inner transducer elements 304 in this subgroup are delayed relative to the outer transducer elements 304, as shown at 316. An ultrasonic beam directed at a point, P, results from the interference of the separate wavelets produced by the subgroup of transducer elements 304. The time delays determine the range, R, which is typically changed during a scan when a two-dimensional image is to be performed. The same time delay pattern is used when receiving the echo signals, resulting in dynamic focusing of the echo signals received by the subgroup of transducer elements 304. In this manner, a single scan line in the image is formed.

To generate the next scan line, the subgroup of transducer elements 304 to be energized are shifted one transducer element 304 position along the length of the transducer array 302 and another scan line is acquired. As indicated at 318, the focal point, P, of the ultrasonic beam is thereby shifted along the length of the transducer 302 by repeatedly shifting the location of the energized subgroup of transducer elements 304.

Figure 14:
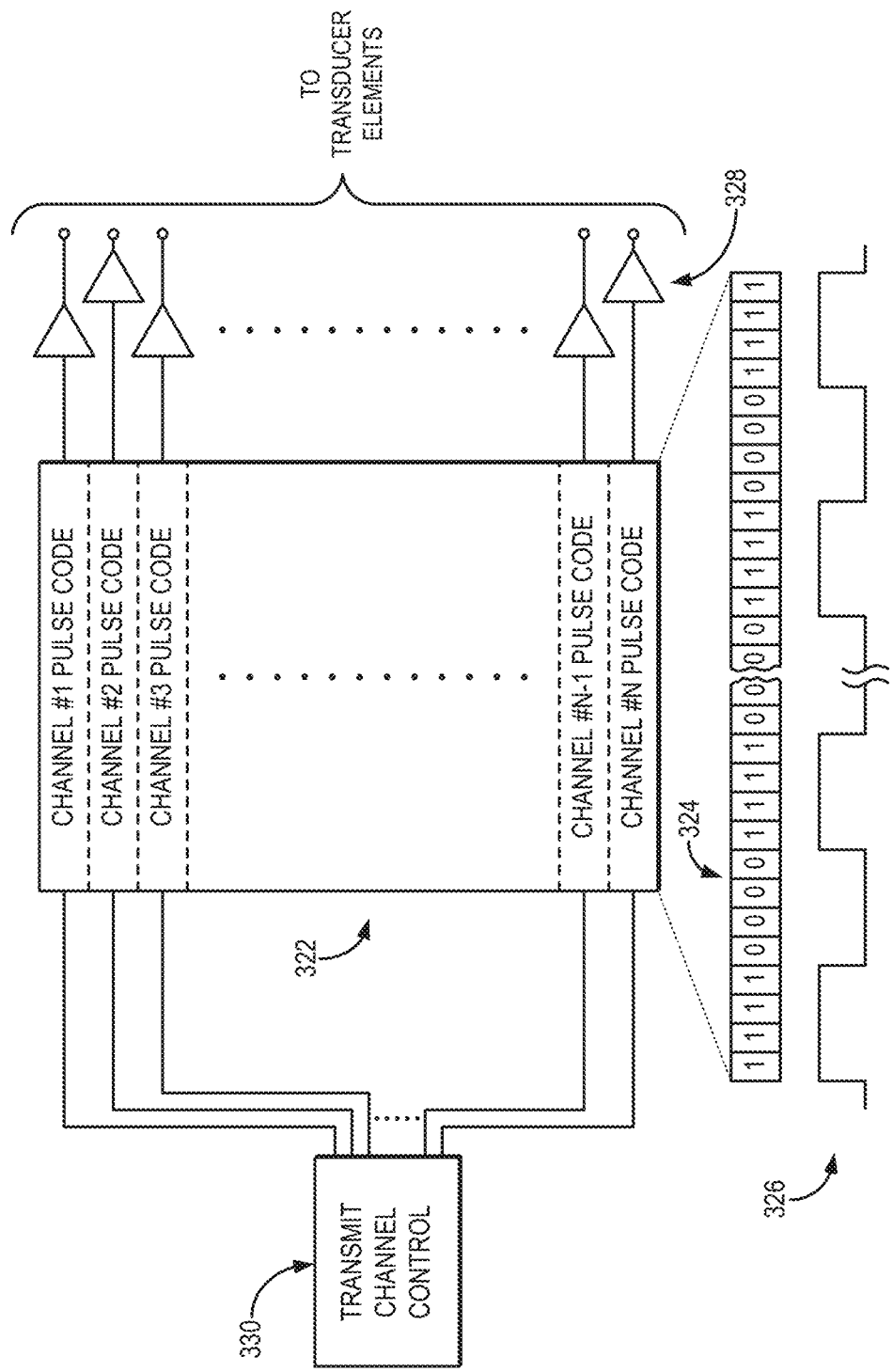
FIG. 14 is a block diagram of an example of a transmitter that forms a part of the ultrasound system of FIG. 13.

Referring particularly to FIG. 14, the transmitter 306 includes a set of channel pulse code memories, which are indicated collectively at 322. In general, the number of pulse code memories 322 is equal to the number of transducer elements 304 in the transducer 302. These pulse code memories are also referred to as transmission channels for this reason. Each pulse code memory 322 is typically a 1×N bit memory that stores a bit pattern 324 that determines the frequency of the ultrasonic pulse 326 that is to be produced. This bit pattern 324 may be read out of each pulse code memory 322 by a master clock and applied to a driver 328 that amplifies the signal to a power level suitable for driving the transducer 302.

Figure 15:
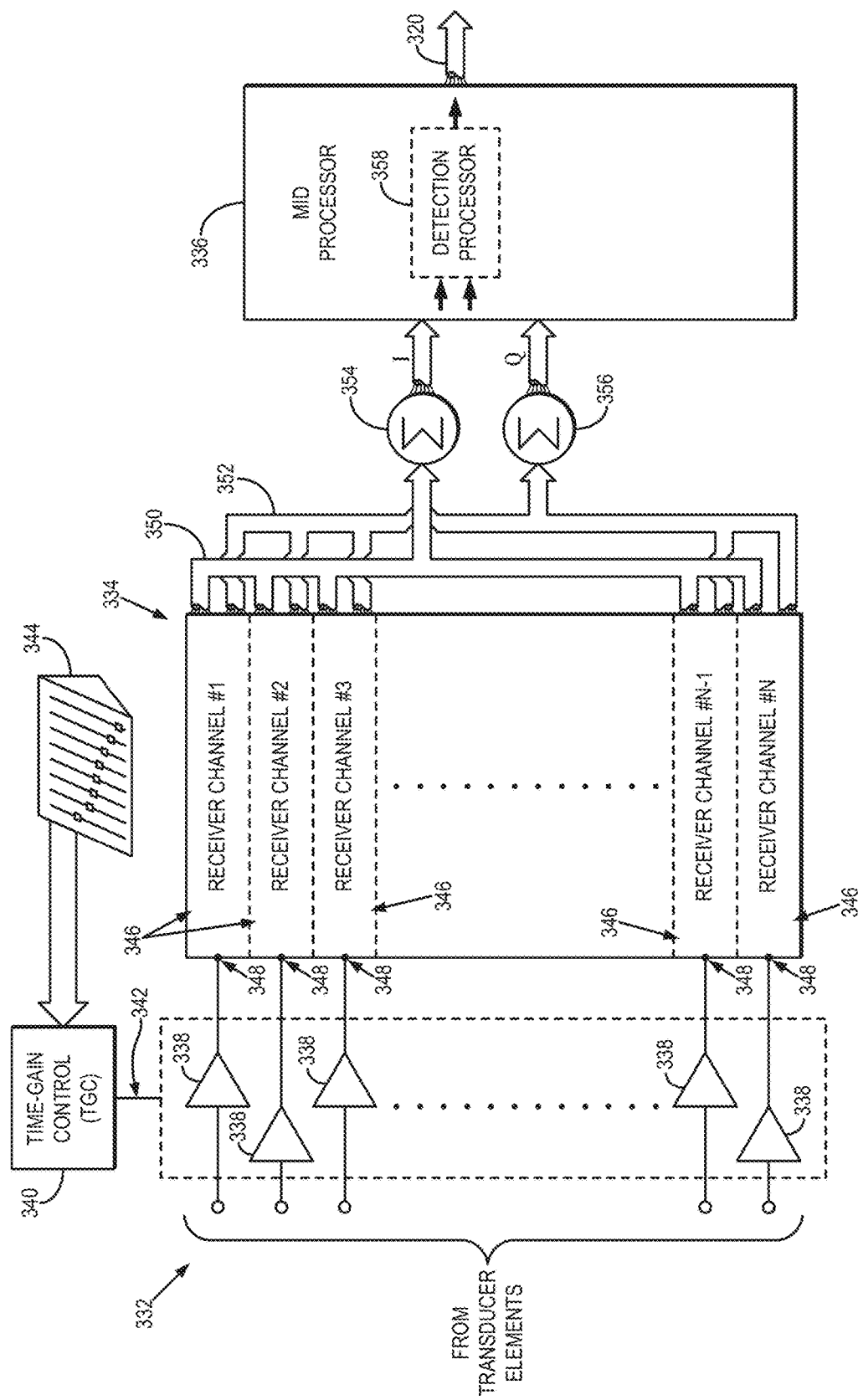
FIG. 15 is a block diagram of an example of a receiver that forms a part of the ultrasound system of FIG. 13.

Referring particularly to FIG. 15, the receiver 308 is comprised of three sections: a time-gain control section 332, a beam forming section 334, and a mid-processor section 336. The time-gain control section 332 includes an amplifier 338 for each receiver channel in the receiver 308, and a time-gain control circuit 340. The input of each amplifier 338 is connected to a respective one of the transducer elements 304 to receive and amplify the echo signal that is receives from the respective transducer element 304. The amount of amplification provided by the amplifiers 338 is controlled through a control line 342 that is driven by the time-gain control circuit 340. As the depth, or range, R, of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by a user who manually sets time-gain control potentiometers 344 to values that provide a relatively uniform brightness over the entire range of the sector scan. The time interval over which the echo signal is acquired determines the range from which it emanates, and this time interval is divided into, for example, eight segments by the time-gain control circuit 340. The settings of the time-gain control potentiometers 344 are employed to set the gain of the amplifiers 338 during each of the respective time intervals so that the received echo signal is amplified in ever increasing amounts over the acquisition time interval.

The beam forming section 334 of the receiver 308 includes a plurality of separate receiver channels 346. As will be explained in more detail below, each receiver channel 346 receives an analog echo signal from one of the amplifiers 338 at an input 348, and produces a stream of digitized output values on an in-phase, I, bus 350 and a quadrature, Q, bus 352. Each of these I and Q values represents a sample of the echo signal envelope at a specific range, R. These samples have been delayed in the manner described above such that when they are summed with the I and Q samples from each of the other receiver channels 346 at summing points 354 and 356, they indicate the magnitude and phase of the echo signal reflected from a point, P, located at range, R, on the steered beam, θ.

The mid-processor section 336 receives beam samples from the summing points 354 and 356. The I and Q values of each beam sample may be, for example, a 16-bit digital number that represents the in-phase, I, and quadrature, Q, components of the magnitude of the echo signal from a point $(R,\theta)$. The mid-processor 336 can perform a variety of calculations on these beam samples, the choice of which is determined by the type of imaging application at task.

The present invention has been described in terms of one or more preferred embodiments, and it should be appreciated that many equivalents, alternatives, variations, and modifications, aside from those expressly stated, are possible and within the scope of the invention.

The invention claimed is:

1. An ultrasound system for measuring material properties of an object comprising:
   an ultrasound transducer that includes a plurality of transducer elements; and
   a processor configured to:
   divide an aperture associated with the plurality of transducer elements into a plurality of segments;
   assign an apodization to each of the plurality of segments, the apodization including assigning a steering angle for each of the plurality of segments;
   based on the apodization, operate the plurality of transducer elements to generate multiple ultrasound push beams that interfere to create multiple foci and multiple shear waves within the object;
   obtain shear wave elastography data from the object; and
   calculate a mechanical property of the object using the obtained elastography data.

2. The system of claim 1 wherein, to assign the apodization, the processor is further configured to assign at least one of a weight to an amplitude of signals applied to elements of the plurality of transducer elements in each of the segments, a steering angle for elements of the plurality of transducer elements in each of the segments, and a focusing delay for elements of the plurality of transducer elements in each of the segments.

3. The system of claim 2 wherein the steering angle includes one of a positive and a negative angle indication.

4. The system of claim 2 wherein the processor is further configured to assign the steering angle using a randomized configuration.

5. The system of claim 1 wherein the processor is further configured to divide the aperture associated with the plurality of transducer elements into a plurality of subapertures for each of the plurality of transducer elements and assign the apodization to each of the subapertures.

6. The system of claim 5 wherein the processor is configured to move or steer each of the subapertures along the aperture to operate the plurality of transducer elements to generate multiple ultrasound push beams.

7. The system of claim 1 wherein the processor is further configured to divide each of the plurality of transducer elements into a number of subgroups with overlapping elements and control activation of the subgroups to move the multiple ultrasound push beams in a lateral direction across the plurality of transducer elements.

8. The system of claim 1 wherein the plurality of transducer elements form one of a linear array or curved array ultrasound transducer or two-dimensional array ultrasound transducer.

9. The system of claim 1 wherein the processor is configured to select the multiple foci using time delays associated with each of the multiple ultrasound push beams.

10. A method for measuring a mechanical property of an object using an ultrasound system having an ultrasound transducer that includes a plurality of transducer elements, the method comprising:
    a) dividing an aperture associated with the plurality of transducer elements into a plurality of segments;
    b) assigning an apodization relative to the plurality of transducer elements, the assigning of the apodization including assigning a steering angle for elements of the plurality of transducer elements in each of the segments;
    c) based on the apodization assigned in b), operating the plurality of transducer elements to generate multiple ultrasound push beams that interfere to create multiple foci and multiple shear waves within the object;
    d) obtaining shear wave elastography data from the object; and
    e) calculating a mechanical property of the object using the obtained elastography data.

11. The method of claim 10 wherein the apodization assigns at least one of a weight to an amplitude of signals applied to elements of the plurality of transducer elements in each of the segments, and a focusing delay for elements of the plurality of transducer elements in each of the segments.

12. The method of claim 11 wherein the steering angle includes one of a positive and a negative angle indication.

13. The method of claim 11 further comprising assigning the steering angle using a randomized configuration.

14. The method of claim 10 wherein b) further comprises dividing an aperture associated with the plurality of transducer elements into a plurality of subapertures for each of the plurality of transducer elements and assigning the apodization to each of the subapertures.

15. The method of claim 14 wherein c) includes moving or steering each of the subapertures along the aperture.

16. The method of claim 10 further comprising dividing each of the plurality of transducer elements into a number of subgroups with overlapping elements and changing the subgroups to move the multiple ultrasound push beams in a lateral direction across the plurality of transducer elements.

17. An ultrasound system for measuring material properties of an object comprising:
    an ultrasound transducer that includes a plurality of transducer elements; and
    a processor configured to:
    divide an aperture associated with the plurality of transducer elements into a plurality of segments;
    assigning a steering angle for elements of the plurality of transducer elements in each of the segments;
    operate the plurality of transducer elements to generate multiple ultrasound push beams by energizing selected ones of the plurality of transducer elements based on the plurality of segments such that the ultrasound push beams interfere to create multiple foci and multiple shear waves within the object;
    obtain shear wave elastography data indicating mechanical properties of the object; and
    generate a report indicating the mechanical properties of the object.

18. The system of claim 17 wherein the mechanical properties include at least one of shear wave speed, shear wave attenuation, shear modulus, shear viscosity, storage modulus, loss modulus, Young's modulus, bulk modulus, or mechanical relaxation time.

19. The system of claim 2 wherein the processor is further configured to assign the steering angle using a deterministic configuration.

20. The method of claim 11 further comprising assigning the steering angle using a deterministic configuration.

* * * * *